United States Patent [19]
Plaut et al.

[11] Patent Number: 5,534,544
[45] Date of Patent: Jul. 9, 1996

[54] SURFACTANTS AND EMULSIFYING AGENTS TO INHIBIT HELICOBACTER

[75] Inventors: Andrew G. Plaut, Lexington; Anne V. Kane, Newton, both of Mass.

[73] Assignee: New England Medical Center Hospitals, Inc., Boston, Mass.

[21] Appl. No.: 293,690

[22] Filed: Aug. 19, 1994

[51] Int. Cl.$^6$ ............................................. A61K 31/23
[52] U.S. Cl. ......................................................... 514/552
[58] Field of Search ..................................... 514/473, 552

[56] References Cited

U.S. PATENT DOCUMENTS

| | | | |
|---|---|---|---|
| 5,248,505 | 9/1993 | Garwin | 424/472 |
| 5,277,902 | 1/1994 | Schmidt et al. | 424/78.37 |

OTHER PUBLICATIONS

Burns, E. M., "An Emulsifying Agent in Digestive Disorders", 1955, *Northwest Med.*, 54:985–87.

CA 111:23100, Klopotek et al., 1987.

Goodwin, C. S., et al., "Unusual Cellular Fatty Acids and Distinctive Ultrastructure in a New Spiral Bacterium (*Campylobacter pyloridis*) From the Human Gastric Mucosa", 1985, *J. Med. Microbiol.* 19:257–67.

Goodwin, C. S., et al., "The Minimum Inhibitory and Bactericidal Concentrations of Antiobiotics and Anti–Ulcer Agents Against Campylobacter Pyloridis", 1986, *J. Antimicrobial Chemotherapy*, 17:309–14.

Hazell, S. L., et al., "Unsaturated Fatty Acids and Viability of Helicobacter (*Campylobacter*) *pylori*", 1990, *J. Clin. Microbiol.*, 28(5):1060–62.

Huesca, M., et al., "Therapeutics Used to Alleviate Peptic Ulcers Inhibit H. *Pylori* Receptor Binding In Vitro", 1993, *Zbl. Bakt.*, 280:244–52.

Knapp, H. R., et al., "Bactericidal Effects of Polyunsaturated Fatty Acids", 1986, *J. Infectious Diseases*, 154(1):84–94.

Marshall, B. J., et al., "Pyloric Campylobacter Infection and Gastroduodenal Disease", 1985, *Med. J. of Australia*, 142(8):439–44.

Millar, M. R., et al., "Bactericidal Activity of Antimocrobial Agents Against Slowly Growing *Helicobacter pylori*", 1992, *Antimocrobial Agents and Chemotherapy*, 36(1):185–87.

Morgan, D. R., et al., "Growth of *Campylobacter pylori* in Liquid Media", 1987, *J. Clin. Microbiol.*, 25(11):2123–25.

Olivieri, R., et al., "Growth of *Helicobacter pylori* in Media Containing Cyclodextrins", 1993, *J. Clin. Microbiol.*, 31(1):160–62.

Secker, D. A., et al., "Gas–Permeable Lifecell Tissue Culture Flasks Give Improved Growth of *Helicobacter pylori* in a Liquid Medium", 29(5):1060–61. (1991).

Shadowen, R. D., et al., "Improved Growth of *Campylobacter pylori* in a Biphasic System", 1989, *J. Microbiol*, 27(8):1744–47.

Xia, H. X., et al., "Enhanced Cultivation of *Helicobacter pylori* in Liquid Media", 1993, *J. Clin. Pathol.*, 46:750–53.

Primary Examiner—Kimberly Jordan
Attorney, Agent, or Firm—Fish & Richardson

[57] ABSTRACT

A method of inhibiting the growth of *Helicobacter pylori* is described. The method involves administering to a mammal a composition containing a surfactant/emulsifying agent and which is substantially free of calcium, magnesium, aluminum and silicon ions.

8 Claims, No Drawings

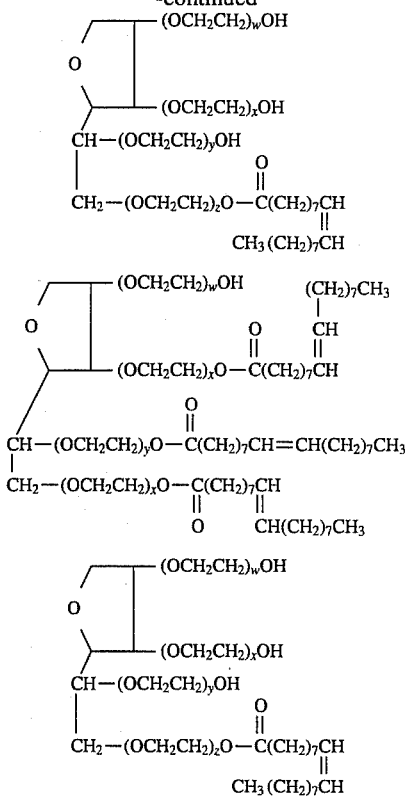

where w+x+y+z have an average value of between 4 and 40, preferably between 4 and 20, and n has a value between 1 and 20, preferably between 10 and 16. Preferably, these sorbitan derivatives are a mixture of, e.g., stearate or oleate esters of sorbitol and sorbitol anhydrides condensed with ethylene oxide, preferably consisting predominantly of the monoester.

The invention also features a method of inhibiting the growth of *Helicobacter pylori* in a mammal by administering a therapeutic composition which contains polyethylene glycol ethers. "Polyethylene glycol ethers" include the class of chemicals having the general formula $R(OCH_2CH_2)_nOH$, where R is an alkyl group attached to PEG by an ether linkage (ROR) and n has an average value between 1 and 100, preferably between 2 and 30.

Another aspect of the invention features a method of treating a patient infected with *Helicobacter pylori* which includes administering sequentially and without overlap an antibiotic with known efficacy against Helicobacter and then administering a biocompatible surfactant/emulsifying agent which is substantially free of calcium, magnesium, aluminum, and silicon ions. This method also excludes the use of concurrent administration with the antibiotic of any surfactant/emulsifying agents, antacids, or antiflatulent pharmaceuticals. Alternatively, the second step of the method (following the standard course of antibiotic therapy) may include the administration of a composition which includes a sorbitan derivative or polyethylene glycol ether.

This invention has uses in the direct treatment of *H. pylori* infections by oral administration of the surfactant/emulsifying agents to the gastric mucosa. Our discovery may also affect the course of currently used ulcer therapy. We have found that surfactant/emulsifying agents have bactericidal activity against *H. pylori* at certain concentrations, whereas at lower concentrations they exert a bacteriostatic effect against *H. pylori* (growth of the bacteria is inhibited, but the bacteria are not killed). Many antibiotics used clinically to treat bacterial infections are only effective against actively growing bacteria, and bacteria which have become static due to exposure to a bacteriostatic agent will not be killed by the antibiotic. Therefore, standard ulcer therapy consisting of antibiotics and antacids administered concurrently could be counterproductive, and treatment with the surfactant/emulsifying agents of this invention might indicate suspension of antibiotic therapy (and vice versa) for the duration of the therapy.

Other features and advantages of the invention will be apparent from the following description of the preferred embodiments thereof, and from the claims.

BRIEF DESCRIPTION OF THE DRAWING

The Figure is a graph showing the growth of *Helicobacter pylori* at 24 hr in modified Brucella broth as influenced by various amounts of fermenter antifoam agents (FIG. 1A) or pharmaceutical anti-gas agents (FIG. 1B). Growth is expressed as a percentage of that in control Brucella medium supplemented with water alone. Each data point is the mean of triplicate cultures, as described below.

DETAILED DESCRIPTION

Reagents

Four commercial antifoam preparations were examined: Antifoam B (Sigma Chemical Corp, St. Louis, Mo.), Antifoam 289 (Sigma), Fermax 27 (Union Carbide Corp., Danbury Conn.), and Medical Antifoam AF (Dow Corning, Midland, Mich.). Octyl polyoxyethylene (OPOE) was generously provided by Dr. Marilyn Loeb. Simethicone was from Aldrich Chemical Co., Milwaukee, Wis.; Carbomer 934P NF Resin from BF Goodrich Co., Cleveland, Ohio; and all other reagents were from Sigma. Gas Relief Drops (Walgreen Corp., Deerfield, Ill.) and Mylicon drops (Johnson & Johnson-Merck Consumer Pharmaceuticals, Fort Washington, Pa.) were purchased in a local pharmacy.

Dilutions of all antifoams and detergents were in sterile distilled water.

Bacterial strains

The *Helicobacter pylori* strains used were clinical gastric isolates, and strains of *H. mustelae*, the species colonizing ferrets, were obtained from Dr. James Fox, Massachusetts Institute of Technology. All study strains were stored in 20% glycerol in Brucella broth at −70° C. and were freshly isolated weekly from frozen stocks.

Methods

*H. pylori* was cultured on solid medium using Campylobacter Agar Skirrow (Difco) plates supplemented with 10% defibrinated sheep's blood (Remel, Lenexa, Kans.) in chambers made microaerobic with the CampyPak system (BBL). Unless otherwise noted, liquid culture medium was Brucella broth (Difco) supplemented with 0.2% cyclodextrin and vancomycin (5 μg/ml). Routine broth cultures were in volumes ranging from 1.5 ml in 16×125 mm borosilicate tubes, to 100 ml cultures in 500 ml capacity borosilicate bottles, all cultured on a platform shaking at 200 rpm in the same microaerobic environment as were agar plates.

Low volume liquid cultures of 100 ml or less were started by inoculation with *H. pylori* obtained by suspending colonies from a 24 hour agar plate into 6 ml supplemented Brucella broth. The $OD_{600}$ of this suspension was measured, and an aliquot sufficient to yield a starting $OD_{600}$ of ~0.1 was inoculated into fresh broth. With this inoculum, these low volume cultures typically reached stationary phase in 24 hours. To initiate a fermenter culture, six such 100 ml

SURFACTANTS AND EMULSIFYING AGENTS TO INHIBIT HELICOBACTER

STATEMENT AS TO FEDERALLY SPONSORED RESEARCH

This invention was made with Government support under grant #DK 34928-09 (awarded by PHS). The Government has certain rights in the invention.

BACKGROUND OF THE INVENTION

The field of the invention is inhibition of growth of the pathogen *Helicobacter pylori*.

*Helicobacter pylori* is a microaerophilic Gram-negative bacterium implicated in several upper gastrointestinal human illnesses including gastritis, duodenal ulcer, and gastric carcinoma (Eurogast Study Group, (1993) Lancet, 341:1359–62; Talley et al., (1991) *J. Natl. Cancer Inst.* 83:1734–9; Wee et al., (1992) Gut 33:1029–32). There are several methods known for culturing this agent in relatively low volumes of 100 ml to 1 L (Hudson, (1989) In: *Gastroduodenal Pathology and Campylobacter pylori*, Megraud and Lamouliane (eds.), p. 11, Elsevier; Millar, (1992) *Antimicrobial Agents and Chemotherapy* 36:185–7; Secker et al., (1991) *J. Clin. Micro.* 29:1060–1; Xia et al., (1993) *J. Clin. Pathol.* 46:750–3).

High volume airflow and agitation required for adequate gas exchange in large volume fermenters create the potential problem of foaming. Foaming is controlled with antifoams added to the culture medium; these typically consist of highly insoluble silicon polymers which are made miscible in water by emulsifying surfactants and/or non-ionic detergents. Simethicone (polydimethylsiloxane) is the silicone polymer used in many commercial antifoams. Antifoams are widely used in the pharmaceutical and biotechnology industries. They are also marketed for relief of intestinal gas, or included in antacids for the same purpose.

Although *Helicobacter pylori* is microaerophilic, successful culture requires stirring and aeration (Goodwin et al., (1986) *J. Antimicro. Chemother.* 7:309–14; Morgan et al., (1987) *J. Clin. Micro.* 25:2123–5; Shadowen et al., (1989) *J. Clin. Micro* 27:1744–7). We found that despite use of conditions reported for large scale liquid culture (Olivieri et al. (*J. Clin. Micro.* 31:160–2), our 5–20 L fermenter batches did not grow.

SUMMARY OF THE INVENTION

We have identified certain constituents of antifoams which are potent growth inhibitors of the pathogenic bacterium *Helicobacter pylori*.

Accordingly, the invention features a method of inhibiting the growth of *Helicobacter pylori* in a mammal by administering to the mammal a biocompatible surfactant/emulsifying agent in a dose sufficient to inhibit *H. pylori*; the administered compound should be substantially free of calcium, aluminum, magnesium, and silicon ions. The term "biocompatible" is used to mean not physiologically harmful, compatible with living tissue or a living system by not being toxic or injurious and not causing immunological reaction. By "substantially free" is meant greater than 95%, and preferably greater than 99% free of the stated contaminating substances.

Preferred surfactant/emulsifying agents are of the general formula $R(OCH_2CH_2)_nOH$, where R can be any alkyl group (preferably $C_{1-20}$) or mixture of alkyl groups attached to the oxygen atom by an ether or ester linkage, and n is an integer between 1 and 100. Other preferred agents include sorbitan alkyl or alkenyl esters that are multiply substituted with polyethylene glycol chains on all free hydroxyl groups.

The preferred homogeneity of the desired agent in a commercially available composition is at least 50%, more preferably 75%, and most preferably greater than 90%, with the contaminants generally being compounds of a closely structurally related compound (e.g., some molecules having both alcohol moieties substituted at either end of the chain).

Examples of suitable surfactant/emulsifying agents include, but are not limited to (e.g., they may or may not have the general formula described above), commercially available agents such as Tween (ICI Americas, Inc.), Triton X (Union Carbide), Brij (ICI Americas, Inc.) detergents, and similar agents including the general chemical classes: alkoxylated carboxylic acids (e.g., polyethylene glycol esters of stearate, laurate, oleate, etc.), alkoxylated alcohols (e.g., polyoxyethylene laurel, stearyl, oleyl, or cetyl ethers), sorbitan derivatives (e.g., polyoxyethylene sorbitan mono-tri stearates, palmitates, oleates or laurates), and ethoxylated alkyl phenols (octylphenoxy polyethoxy ethanols).

Preferably, the surfactant/emulsifying agents will have between 2 and 30 repeats (lower molecular weights), exclusive of the "R" group defined above, to facilitate their suspension in a carrier compound. Less preferably, agents with more than 30 repeats may be used.

A preferred surfactant/emulsifying agent is a polyethylene glycol (PEG) stearate, which is at least 50% pure PEG 8 or PEG 20 stearate. "50% pure" in this context means that 50% of the PEG stearate molecules in the therapeutic composition are the desired PEG stearate species. Less preferably, other lengths and mixtures of lengths of PEG chains may be used. The PEG stearate generally will be present in a physiologically acceptable carrier, e.g., distilled water, in a concentration range between 0.001% and 80% by volume, more preferably between 0.1% and 10%.

Another suitable surfactant/emulsifying agent is polyoxyethylene (20) sorbitan monooleate or polyoxyethylene (20) sorbitan monolaurate, e.g., the commercial detergents Tween 80 and Tween 20 (Union Carbide).

The invention also features a method of inhibiting the growth of *Helicobacter pylori* in a mammal by administering a therapeutic composition which contains sorbitan derivatives. By "sorbitan derivative" is meant the class of chemicals having generally one of the following formulas

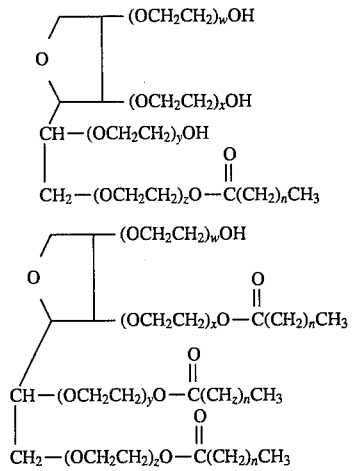

cultures ($OD_{600}$ ~1.5–2.0) were used to inoculate each 10 L of fermenter medium. Fermenter cultures were in a MF128S apparatus (New Brunswick Scientific, Edison, N.J.) at 37° C. in an atmosphere produced by introducing a gas mixture of 5% $O_2$, 5% $CO_2$, and 90% $N_2$ maintained at a flow rate of 3–4 L/min. Agitation was at 150–300 rpm and was periodically adjusted to sustain a dissolved oxygen saturation of ~15% of maximum (the dissolved oxygen probe was calibrated to 100% before culture using an airflow of 20 L/min and agitation rate of 200 rpm).

The effect of antifoams and related compounds on *Helicobacter pylori* growth was measured as follows. Supplemented Brucella broth was inoculated with bacterial suspension to $OD_{600}$ ~0.1, as described above. Ten ml aliquots of the suspension received 10 μl of a dilution of either antifoam or detergent, and a control tube received only distilled water. Triplicate 1.5 ml samples from the Helicobacter/antifoam suspensions were placed into individual borosilicate tubes and the zero time $OD_{600}$ was measured on the remainder. All tubes were incubated together at 37° C. in a single chamber on a platform rotating at 200 rpm. Growth at 24 h was assessed by measurement of $OD_{600}$ of each tube. Preliminary experiments showed a linear relationship between $OD_{600}$ and colony forming units (cfu)/ml over the range of 0.1–1.0. The influence of antifoam or detergent on growth was expressed as a percentage of control, calculated by subtracting $OD_{600}$ at zero time from the final value for each tube, and taking as 100% growth the value in cultures containing water diluent only. An $ID_{50}$ was determined for each antifoam or detergent (Table 1) by generating multiple dose response curves for each inhibitor, narrowing the set of dilutions to find a range of inhibition clustered around 50% of control.

To obtain minimum bactericidal concentrations (MBCs), colony counts were performed on cultures before and after 24 h incubation with antifoam or detergent. Samples were serially diluted in supplemented Brucella broth, triplicate 20 μl aliquots were plated on Campy/blood agar plates, and colonies were counted following 72 h culture in a microaerobic chamber.

Results

All four antifoams markedly inhibited growth of *Helicobacter pylori* (FIG. 1A); all suppressed cell growth at 10 ppm (volume/volume, approximately 10 μg/ml), by at least 90%, and two showed partial growth inhibition at 1 μg/ml. Growth suppression by antifoam also occurred in brain heart infusion supplemented with cyclodextrin, and brucella broth supplemented with 10% fetal calf serum instead of cyclodextrin (data not shown). Growth of five *H. pylori* strains in addition to the prototype Leung strain reported in Table 1 and the Figure were similarly inhibited. In contrast, growth of two strains of *Helicobacter mustelae* in liquid medium were only affected by Antifoam B at concentrations above 1000 μg/ml.

To take advantage of the finding that antifoams impaired *Helicobacter pylori* proliferation, we cultured large fermenter batches without antifoams. These were at 10 L, half the maximum chamber capacity, to accommodate the expected foam. Four separate fermentations of this size all had excellent cell growth, reaching stationary phase $OD_{600}$ of 2.32±0.25 in 24 h. Log phase doubling time in the absence of antifoam was 5 h.

We also examined pharmaceutical antifoam preparations that contain simethicone/detergent emulsions. Walgreen's Gas Relief drops and Mylicon, each containing 40 mg simethicone/0.6 ml were tested in dose response experiments. Both compounds inhibited growth of *Helicobacter pylori* (FIG. 1B). At higher doses, Mylicon was also found to be bactericidal, with $MBC_{90}$ of 1000 μg/ml. The Walgreen product was also bactericidal, but an MBC was not determined.

We then undertook to identify the growth inhibiting principle in these various compounds. Table 1 shows $ID_{50}$ values for all tested materials including antifoams used in fermenters, pharmaceutical antifoams, and emulsifiers. Simethicone itself is water insoluble, and could not be individually tested. In attempts to bring simethicone into a stable emulsion we used various laboratory detergents, and these were first separately tested as Helicobacter growth inhibitors. Table 1 shows that all inhibited growth, but Tween 20 (polyoxyethylene sorbitan monolaurate) and Tween 80 (polyoxyethylene sorbitan monooleate) were at least tenfold more inhibiting than were Nonidet P40, Triton X100, and OPOE. We then tested carboxymethylcellulose and Carbomer 934P, suspending agents in the Walgreen and Mylicon products, respectively, and these did not inhibit growth. However, Dow Corning Medical Antifoam, already found to be strongly inhibiting (see above), is the source of simethicone in Mylicon and contains additional emulsifiers, one of which is polyethylene glycol (PEG) stearate. This compound can be synthesized in varying chain lengths. We chose PEG 8 stearyl ether and PEG 20 stearyl ether for dose response experiments. *H. pylori* was found to be markedly sensitive to these detergents. The $ID_{50}$s of PEG 8 stearyl ether and PEG 20

TABLE 1

Dose (μg/ml) of various agents that suppress by half the growth of *Helicobacter pylori*, strain Leung.

|  | $ID_{50}$ (μg/ml) |
|---|---|
| Antifoams used in fermenters* | |
| Antifoam B (10-500) | 0.5 |
| Antifoam 289 (100) | 0.65 |
| Fermax 27 (100-250) | 7.0 |
| Dow Corning Medical Antifoam (2-50) | 1.3 |
| Therapeutic antifoams | |
| Walgreen's | 3.5 |
| Mylicon | 4.2 |
| Emulsifiers/detergents | |
| SDS | 32 |
| NP40 | 34 |
| Triton X100 | 27 |
| OPOE | 13 |
| Tween 20 | 0.4 |
| Tween 60 | 0.1 |
| Tween 80 | 0.6 |
| carboxymethylcellulose | >100 |
| Carbomer 934P | >100 |
| PEG 8 stearyl ether | 0.016 |
| PEG 20 stearyl ether | 0.031 |

*The $ID_{50}$ values were obtained by extrapolation from dose-response curves. Concentrations of all material tested is based on wt/vol for solid compounds, and vol/vol for liquids.
The manufacturer's recommended doses (μg/ml) for fermenters are in parentheses for each fermenter antifoam.

stearyl ether were 0.016 and 0.031 μg/ml, respectively, while the growth of *E. coli*, *H. influenzae*, and *S. aureus* was unaffected by PEG 8 stearyl ether at concentrations of 100 μg/ml. These compounds were also bactericidal to *H. pylori*, PEG 8 stearyl ether having an $MBC_{90}$ of 4 μg/ml, and PEG 20 10 μg/ml.

We then tested simethicone itself as an inhibitor, overcoming its water insolubility by emulsifying the material as 10% solutions in Carbomer 934P or in NP40. Simethicone so formulated did not cause the growth inhibition seen with either emulsifier alone (two tailed t-test). Also, addition of more simethicone to Mylicon or to PEG 8 stearyl ether and PEG 20 stearyl ether solutions (emulsified and then diluted to concentrations giving 10–50% inhibition) failed to increase growth inhibition by these emulsifiers. These experiments indicated that simethicone was not the growth inhibiting component in antifoam agents.

Discussion

Our data indicate that antifoams commonly added to large scale bacterial culture in fermenters inhibit the proliferation of *H. pylori*, and were identified as the sole factor in our inability to scale up culture volumes of this gastric pathogen from 100 ml, in which it grew well, to over 1 L. All of four commercial antifoams we examined inhibited Helicobacter growth, and their elimination from culture removed growth suppression.

For fermenter culture we used the medium that was developed to provide a serum substitute for *H. pylori* culture (Olivieri et al. (*J. Clin. Micro.* 31:160–2)). Cell doubling time using this medium in a fermenter was reported to be approximately 16–18 hrs during log phase, and bacterial numbers reached a maximum at 128 hrs. We assume that antifoam was added to those fermenter cultures in keeping with standard practice. Our experience with the same medium, but antifoam-free, showed log phase doubling time in a fermenter of 5 hours and maximum cell numbers in 24 hrs. We conclude that antifoam elimination leads to faster growth.

Uses/Advantages

The results reported here have clinical importance. The usual dose of Mylicon, even if diluted with one liter of volume in the stomach, would not be diluted beyond its MBC. Thus gastric levels of simethicone emulsions reached with recommended doses of these antiflatulents may kill *H. pylori*, or inhibit its growth. Aside from direct cidal effects of pharmaceutical antifoams on *H. pylori*, growth suppression could also interrupt the efficacy of bactericidal antibiotics (e.g., amoxicillin) used to treat these infections. There is evidence that slowly dividing Helicobacter are less susceptible to antibiotic eradication (Millar, (1992) *Antimicrobial Agents and Chemotherapy* 36:185–7). Antibiotic treatment failure may be in part related to concomitant use of growth suppressive antifoams found in antacids, suggesting that it may become necessary to recommend a temporary suspension of their use during the standard regimen of antimicrobial therapy.

The surfactant/emulsifying agents of the invention may be formulated in any physiologically suitable composition for oral administration to a patient, but should not contain the metal ions (calcium, aluminum, magnesium) commonly used to inhibit gastric acid secretion or the inert ingredient simethicone. The optimal concentration of the active agent (the surfactant/emulsifying agent) can be easily determined using the methodology described above (dose-response curves of the agent compared to untreated control cultures in the linear growth range ($OD_{600}$=0.1–1.0)). A concentration of 1 to $10^7$ times the calculated $ID_{50}$ can be used in the therapeutic. This will account for dilution of the agent by the patient's stomach volume and compensate for a short residence time in the stomach. Greater concentrations may also be used. For instance, an effective concentration of PEG stearate might be as low as 0.0001%, although concentrations of 2.2% or higher of PEG stearates are found in existing pharmaceuticals, and would not be toxic in the compositions of the invention.

Compositions of the invention may be administered in any suitable excipient (e.g., sterile water, buffered saline). They may also be made in slow-release formulations to enhance drug delivery over time, using, for example, a polymer or carbohydrate matrix, liposomes, or any other delivery/release system known to one skilled in that art.

What is claimed is:

1. A method for inhibiting the growth of *Helicobacter pylori* in a mammal, said method comprising orally administering to said mammal a composition comprising polyethylene glycol stearate, said composition being substantially free of calcium, magnesium, aluminum, and silicon ions.

2. The method of claim 1 wherein the molecular species of said polyethylene glycol stearate is at least 50% PEG stearate 8 or PEG stearate 20.

3. A method for inhibiting the growth of *Helicobacter pylori* in a mammal, said method comprising orally administering to said mammal a composition comprising sorbitan alkyl or alkenyl ester which is multiply substituted with polyethylene glycol chains on all free hydroxyl groups, said composition being substantially free of calcium, magnesium, aluminum, and silicon ions.

4. A method for inhibiting the growth of *Helicobacter pylori* in a mammal, said method comprising orally administering to said mammal a composition comprising a polyethylene glycol ether, said composition being substantially free of calcium, magnesium, aluminum, and silicon ions.

5. A method for inhibiting the growth of *Helicobacter pylori* in a mammal, said method comprising orally administering to said mammal a composition comprising a polyethylene glycol stearyl ether, said composition being substantially free of calcium, magnesium, aluminum, and silicon ions.

6. The method of claim 5 wherein the molecular species of said polyethylene glycol stearyl ether is at least 50% PEG 8 stearyl ether or PEG 20 stearyl ether.

7. A method for inhibiting the growth of *Helicobacter pylori* in a mammal, said method comprising orally administering to said mammal a composition comprising a polyethylene glycol alkyl ether, said composition being substantially free of calcium, magnesium, aluminum, and silicon ions.

8. A method for inhibiting the growth of *Helicobacter pylori* in a mammal, said method comprising orally administering to said mammal a composition comprising a polyethylene glycol ester, said composition being substantially free of calcium, magnesium, aluminum, and silicon ions.

\* \* \* \* \*